United States Patent
Leal et al.

(10) Patent No.: US 9,552,459 B2
(45) Date of Patent: Jan. 24, 2017

(54) METHOD AND APPARATUS FOR IMPLEMENTING A TASK PLAN INCLUDING TRANSMISSION OF ONE OR MORE TEST MESSAGES

(71) Applicant: McKesson Financial Holdings, Hamilton (BM)

(72) Inventors: David Leal, San Francisco, CA (US); Brian Wuollet, Cumming, GA (US); Somnath Lokesh, Pleasanton, CA (US); Dominique Plante, Martinez, CA (US); Jordan Liu, Castro Valley, CA (US); Svetlozar Petrov, Emeryville, CA (US); Evan Schnell, San Rafael, CA (US)

(73) Assignee: McKesson Financial Holdings, Hamilton (BM)

(*) Notice: Subject to any disclaimer, the term of this patent is extended or adjusted under 35 U.S.C. 154(b) by 173 days.

(21) Appl. No.: 14/149,334

(22) Filed: Jan. 7, 2014

(65) Prior Publication Data

US 2015/0195724 A1   Jul. 9, 2015

(51) Int. Cl.
*G06F 9/44* (2006.01)
*G06F 19/00* (2011.01)
*G06F 11/36* (2006.01)

(52) U.S. Cl.
CPC ....... *G06F 19/3418* (2013.01); *G06F 11/3664* (2013.01); *G06F 19/3412* (2013.01); *G06F 19/366* (2013.01)

(58) Field of Classification Search
USPC ................. 717/124–125, 127, 131
See application file for complete search history.

(56) References Cited

U.S. PATENT DOCUMENTS

| | | | |
|---|---|---|---|
| 6,185,701 B1* | 2/2001 | Marullo | G06F 17/3089 707/E17.116 |
| 7,055,137 B2* | 5/2006 | Mathews | G06F 11/3688 714/46 |
| 7,992,133 B1* | 8/2011 | Theroux | G06F 11/362 709/201 |
| 2004/0015846 A1* | 1/2004 | Haisraeli | G06F 9/52 717/115 |

(Continued)

OTHER PUBLICATIONS

Office Action from Canadian Patent Application No. 2,876,450 dated Dec. 10, 2015.

*Primary Examiner* — Jason Mitchell
(74) *Attorney, Agent, or Firm* — Alston & Bird LLP

(57) ABSTRACT

A method, computing device and computer program product are provided in order to implement a test plan in an efficient manner. In the context of a method, a plurality of test messages from each of a plurality of different source systems are stored. The plurality of test messages may include test messages to be captured in an electronic health record. The method constructs a test plan. The test plan identifies an end point. The test plan also includes one or more test messages that have been previously stored and respective anticipated outcomes at the end point following transmission of the test messages. The method also includes transmitting the test messages of the test plan and receiving feedback regarding the outcome following transmission of the test messages of the test plan to the end point. The method also includes determining whether the test plan was successfully executed based upon the feedback.

24 Claims, 11 Drawing Sheets

(56) References Cited

U.S. PATENT DOCUMENTS

| | | | |
|---|---|---|---|
| 2005/0060610 A1* | 3/2005 | Leary | G06F 11/3672 714/25 |
| 2006/0259325 A1* | 11/2006 | Patterson | G06Q 10/10 705/2 |
| 2008/0066009 A1* | 3/2008 | Gardner | G06F 8/34 715/809 |
| 2011/0289489 A1* | 11/2011 | Kumar et al. | G06F 11/3664 717/135 |
| 2012/0059668 A1* | 3/2012 | Baldock | G06Q 10/10 705/3 |
| 2014/0100877 A1* | 4/2014 | Rennicks | G06Q 10/06 705/3 |
| 2015/0169432 A1* | 6/2015 | Sinyagin | G06F 11/3684 717/124 |

* cited by examiner

| Interface Project: | I-0001234 |
|---|---|
| Project Manager | |
| Interface Number | |
| Description | |
| Interface Type | |
| Health System | |
| Source System | |
| End Point System | |
| Practice ID | |

Customer Testing Date

| Start Date | |
|---|---|
| Due Date | |

Test Plan and Test Scenarios

Interface Project:    I-0001234

Project Manager

Interface Number

Description

Interface Type

Health System

Source System

End Point System

Practice ID

Customer Testing Date

42

44

| Test Plan and Test Scenarios | | |
|---|---|---|
| Test Plan – The Clinic of Hope Prelims | | |
| Scenario Name | Expected Outcome | Status |
| CBC Prelim | Results not displayed and be filtered from view | |
| Sodium Non-Prelim | Results should pass and display regular values | |

Figure 7

Create Scenario By Adding Messages

Messages in Source System: IDP-24-GVM

☐ Select/Unselect All

☐ Message 1: Details ⸺⸺⸺⸺ 52

[goldenvalley_in ×] [IDP-22 ×] [IDP-24 ×] [IDP-26 ×]  add a tag

Save Tags

Reserved Tag Legend:
F: Final
P: Preliminary
C: Corrected
X: Cancelled

Message

```
MSH|^~\&|IDP-24|GVM.TEST5.65|RPT.IIR|IIR|201210311742||ORU^R01|1050988540.1.37|D|2.3|||AL||||
EVN|R01|201210311742||||
PID|1||M000000062||GOLDEN^FRUIT^^^^||19760209|F|||100 APPLE LN^^COLLINS^MO^64738||(816)251-9999^^^^816^2519999||||V000000000810|123-45-123
4|||||||||||
PV1|1|O|LAB^^^GVM|EL|||1851323901^BELLAMY^BRIAN^^^^MD|||||||||CLI||U||||||||||||||||||GVM||REG CLI|||201210311739|||||||
TXA|1|DI|FT|201210311741||201210311741|201210311741|201210311742|^MEDITECH^DOCTOR^F^^^^^^^^^^NPI||JS853^SRCH^JEAN^^^^|201210311-0001|||
20121031-0001|AU||AV|||^MEDITECH^DOCTOR^F^^^^^^^^^^NPI^^201210311742|
ORC|RE|||||CM|1||201210311742|JS853^SRCH^JEAN^^^^|||||||||
OBR|1||||||||||201210311741||||||201210311741|||F||1|||||^MEDITECH^DOCTOR^F^^^|
OBX|1|TX|^|| GOLDEN VALLEY MEMORIAL HEALTHCARE ||||||P||||||
OBX|2|TX|^|| Department of Diagnostic Imaging |||||P||||||
OBX|3|TX|^|| 1600 North Second Street |||||P||||||
OBX|4|TX|^|| Clinton, MO 64735 |||||P||||||
OBX|5|TX|^|| (660) 890-7145 |||||P||||||
OBX|6|TX|^||  |||||P||||||
OBX|7|TX|^||  |||||P||||||
```

52 ⸺

☐ Message 2: Details

[goldenvalley_in ×] [IDP-22 ×] [IDP-24 ×] [IDP-26 ×] [FINGER L ×] [FINGER LEFT ×]  add a tag Save Tags

Reserved Tag Legend:
F: Final
P: Preliminary
C: Corrected
X: Cancelled

Message

```
MSH|^~\&|IDP-24|GVM.TEST5.65|RPT.IIR|IIR|201303211738||ORU^R01|1043170200.1.226|D|2.3|||AL||||
EVN|R01|201303211738||||
PID|1||M000000003||TEST^FRANKLIN^A^^^||19881215|M||W|1818 N POND LANE^^CLINTON^MO^64735||(660)885-1155^^^^^660^8851155|||S||V000000003483|44
5-77-6655|||||||||
PD1||||1033187877^CLOUSE^JAMES^C FACOI FACNP^^^DO|
PV1|1|O|OP.CNTR^^^GVM|EL|||^MEDITECH^DOCTOR^F^^^||||||PHY|||CLI||SP|||||||||||||||||GVM||REG CLI|||201301301143|||||||1184656076^SCOTT
^KEN^^^MD|
```

METHOD AND APPARATUS FOR IMPLEMENTING A TASK PLAN INCLUDING TRANSMISSION OF ONE OR MORE TEST MESSAGES

TECHNOLOGICAL FIELD

An example embodiment of the present invention relates generally to the implementation of a test plan including the transmission of one or more test messages and, more particularly, the implementation of a test plan that includes the transmission of one or more test messages that are to be captured in an electronic health record.

BACKGROUND

Modern healthcare requires the interconnectivity of a number of disparate systems. For example, physician practices and laboratories must repeatedly communicate to allow a physician to order one or more tests and for the laboratories to report the results of those tests. In order to permit these disparate systems to connect and communicate with one another, an interface is generally positioned between the disparate systems to facilitate their integration.

Prior to commencing commercial use of an interface to connect multiple disparate systems, the interface is generally tested to ensure that the interface and the resulting intersystem connectivity satisfies the various requirements. These requirements may include, for example, workflow, data integrity and regulatory requirements. In order to test the interface, several stakeholders who are members of different organizations must typically participate, thereby resulting in coordination challenges for the resources required to test the interface.

By way of example in which an interface is intended to support the connectivity between a laboratory and a physician practice, representatives of the laboratory, the physician practice and, in some instances, the electronic health record vendor of the physician practice must meet so as to design the test plan via which the interface will be tested. Thereafter, the laboratory must transmit a plurality of test messages to the physician's practice and the physician's practice, in turn, must evaluate the resulting electronic health record to determine if the test messages were properly received and acted upon. If so, the interface may be considered to be functioning properly. However, if the test messages are not properly received, the interface may be considered to have failed such that further evaluation may be conducted prior to the commercial launch.

As the foregoing example demonstrates, the testing of an interface generally requires the cooperation and the devotion of time and resources concurrently by members of several different organizations. It may sometimes prove challenging to obtain the requisite resources from the various organizations and, in any event, may be even more challenging to coordinate the concurrent availability of those resources in order to property test the interface.

BRIEF SUMMARY

A method, computing device and computer program product are provided in accordance with an example embodiment in order to implement a test plan in an efficient manner. In this regard, the method, computing device and computer program product of an example embodiment may permit a plurality of test messages to be stored in advance of the execution of the test plan. As such, the test plan may thereafter be executed without requiring the concurrent participation of members from both the source system and the end point. For example, in an instance in which the communication between a laboratory and a physician practice is to be evaluated, test messages from the laboratory may be stored such that the test plan may be subsequently executed with little or no involvement by the laboratory during the test. As a result, the method, computing device and computer program product of an example embodiment may permit an interface to be tested pursuant to a test plan in a manner that creates less of an imposition upon the participants and, in some embodiments, may completely eliminate the need for participation by the members of one of the source system or the end point during the test, while still resulting in a fulsome evaluation of the interface. Indeed, the method, computing device and computer program product of an example embodiment may permit an interface to be comprehensively tested.

In one embodiment, a method is provided that includes storing a plurality of test messages from each of a plurality of different source systems. The plurality of test messages may include test messages, such as health level 7 (HL7), Continuity of Care document (CCD) or fast healthcare interoperability records (FHIR) test messages, to be captured in an electronic health record. The method of this embodiment also constructs, with processing circuitry, a test plan. The test plan identifies an end point. The test plan also includes one or more test messages that have been previously stored and respective anticipated outcomes at the end point following transmission of the one or more test messages. For example, the respective anticipated outcomes may include respective anticipated modifications to the electronic health record. The method of this example embodiment also includes transmitting the one or more test messages of the test plan and receiving feedback regarding the outcome following transmission of the one or more test messages of the test plan to the end point. The method of this embodiment also includes determining whether the test plan was successfully executed based upon the feedback.

The construction of the test plan may include constructing a test plan that includes one or more test scenarios. Each test scenario may include one or more test messages and respective anticipated outcomes at the end point following transmission of the one or more test messages. In an instance in which the test plan includes a plurality of test scenarios, the method of an example embodiment may transmit the one or more test messages of at least one test scenario of the test plan and defer transmission of the one or more test messages of another test scenario of the test plan. The method of an example embodiment may also include associating tags with respective test messages that have been stored. In this example embodiment, the method may construct the test plan by identifying the one or more test messages of the test plan based upon tags associated with the respective test messages.

In another embodiment, a computing device is provided that includes processing circuitry configured to cause storage of a plurality of test messages from each of a plurality of different source systems. The plurality of test messages includes test messages to be captured in an electronic health record, such as health level 7 (HL7), Continuity of Care document (CCD) or fast healthcare interoperability records (FHIR) test messages. The processing circuitry of this embodiment is also configured to construct a test plan identifying an end point. The test plan also includes one or more test messages that have been previously stored and respective anticipated outcomes at the end point following transmission of the one or more test messages. For example, the respective anticipated outcomes may include respective anticipated modifications to the electronic health record. The processing circuitry of this embodiment is also configured to cause transmission of the one or more test messages of the test plan and to receive feedback regarding the outcome following transmission of the one or more test messages of the test plan to the end point. The processing circuitry of this embodiment is also configured to determine whether the test plan was successfully executed based upon the feedback.

The processing circuitry of an example embodiment is configured to construct the test plan by constructing a test plan including one or more test scenarios. Each test scenario includes one or more test messages and respective anticipated outcomes at the end point following transmission of the one or more test messages. In an embodiment in which the test plan includes a plurality of test scenarios, the processing circuitry may be configured to cause transmission of the one or more messages of at least one test scenario of the test plan and to defer transmission of the one or more test messages of another scenario of the test plan. The processing circuitry of an example embodiment may be further configured to associate tags with respective test messages that have been stored. In this embodiment, the processing circuitry is configured to construct a test plan by identifying the one or more test messages of the test plan based upon tags associated with the respective test messages.

In a further embodiment, a computer program product is provided that includes a non-transitory computer readable medium having program code stored thereon with the program code including program code instructions configured, upon execution, to cause storage of a plurality of test messages from each of a plurality of different source systems. The plurality of tests messages include test messages to be captured in an electronic health record, such as health level 7 (HL7), Continuity of Care document (CCD) or fast healthcare interoperability records (FHIR) messages. The program code of this embodiment also include program code instructions configured, upon execution, to construct a test plan identifying an end point. The test plan also includes one or more test messages that have been previously stored and respective anticipated outcomes at the end point following transmission of the one or more test messages. For example, the respective anticipated outcomes may include respective anticipated modifications to the electronic health record. The program code of this embodiment also includes program code instructions configured to cause transmission of the one or more test messages of the test plan and to receive feedback regarding the outcome following transmission of the one or more test messages of the test plan to the end point. The program code of this embodiment also includes program code instructions configured to determine whether the test plan is successfully executed based upon the feedback.

The program code instructions configured to construct the test plan may include program code instructions configured to construct a test plan that includes one or more test scenarios. Each test scenario includes one or more test messages and respective anticipated outcomes at the end point following transmission of the one more test messages. In an embodiment in which the test plan includes a plurality of test scenarios, the program code instructions configured to cause transmission of the one or more test messages of the test plan may include program code instructions configured to cause transmission of the one or more test messages of at least one test scenario of the test plan and to defer transmission of the one or more test messages of another test scenario of the test plan. The program code of another embodiment may further include program code instructions configured to associated tags with respective test messages that have been stored. In this embodiment, the program code instructions configured to construct the test plan may include program code instructions configured to identify the one or more test messages of the test plan based upon tags associated with the respective test messages.

BRIEF DESCRIPTION OF THE DRAWINGS

Figure 1:
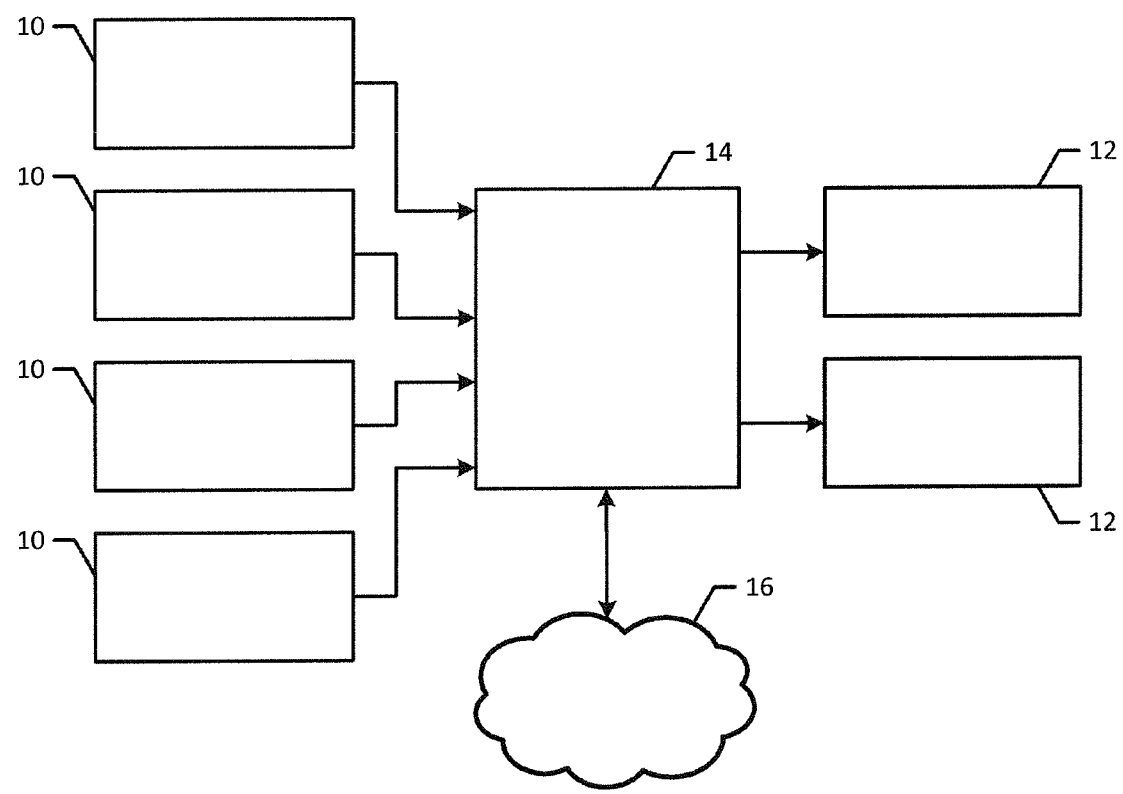
Figure 2:
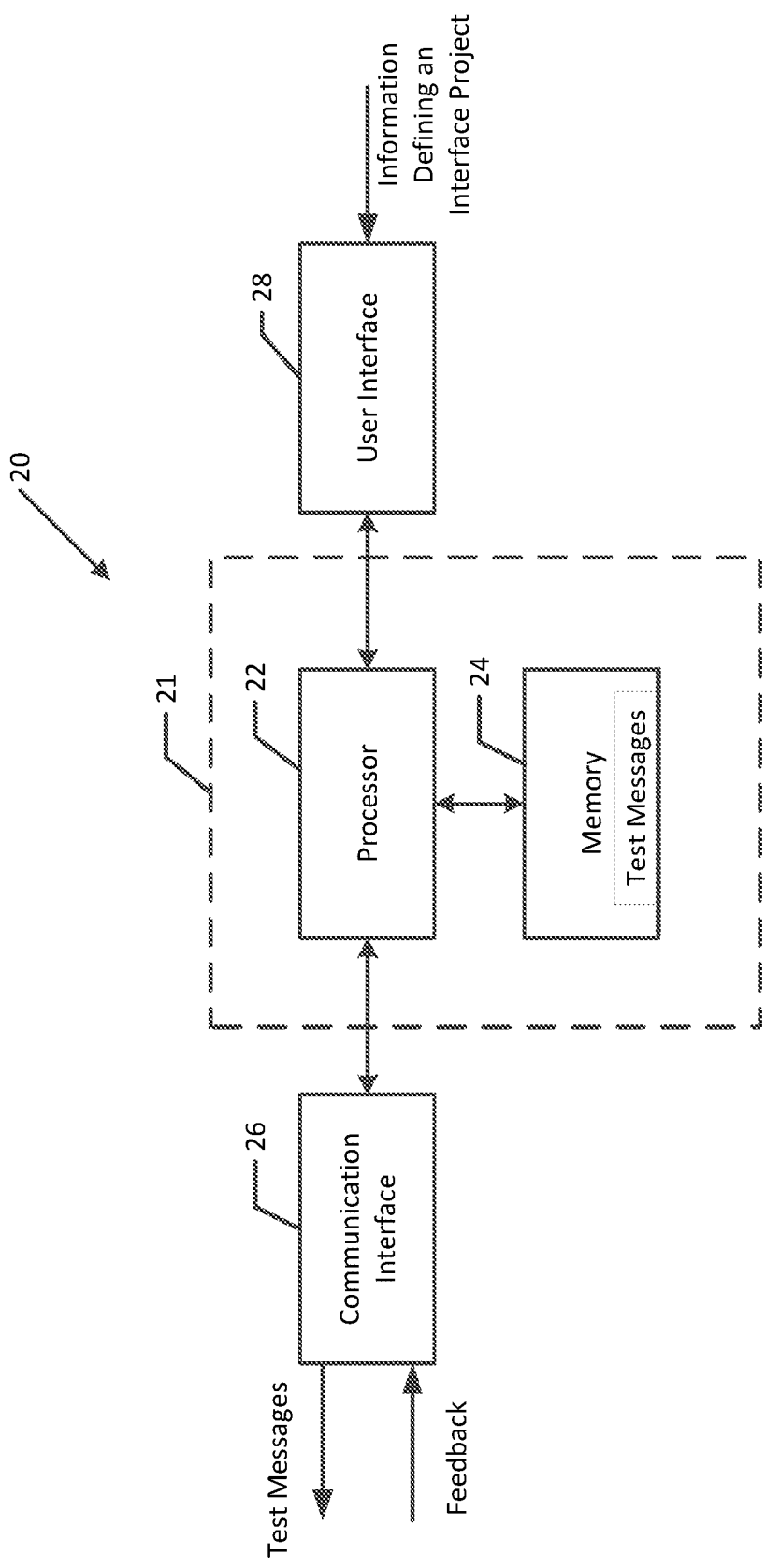
Figure 3:
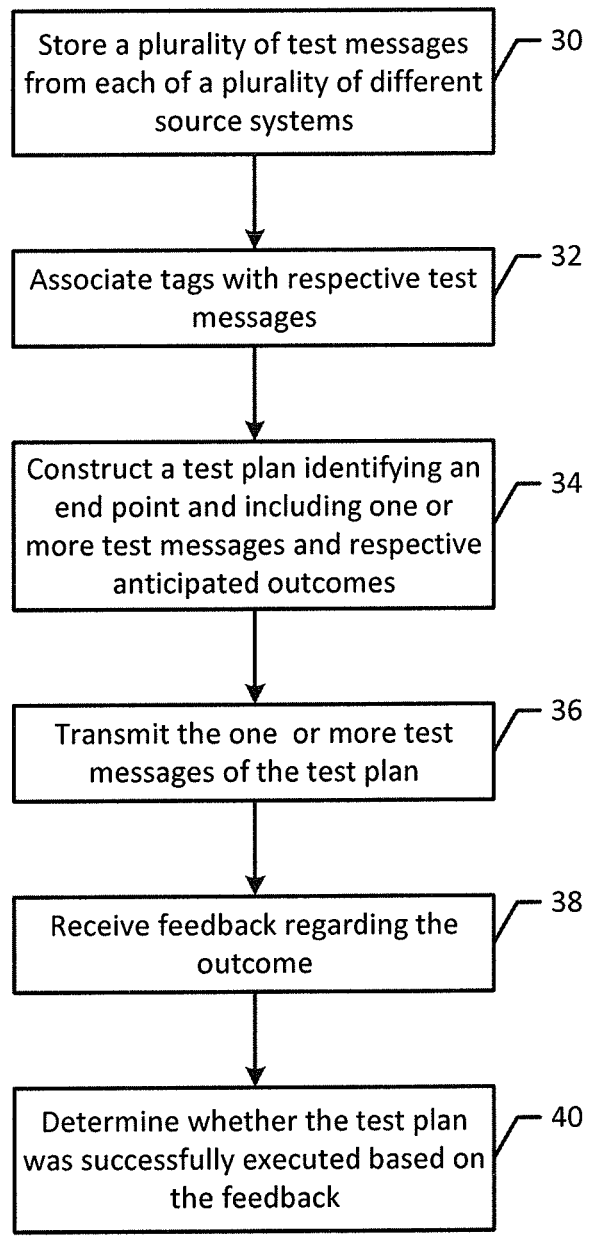
Figure 5:
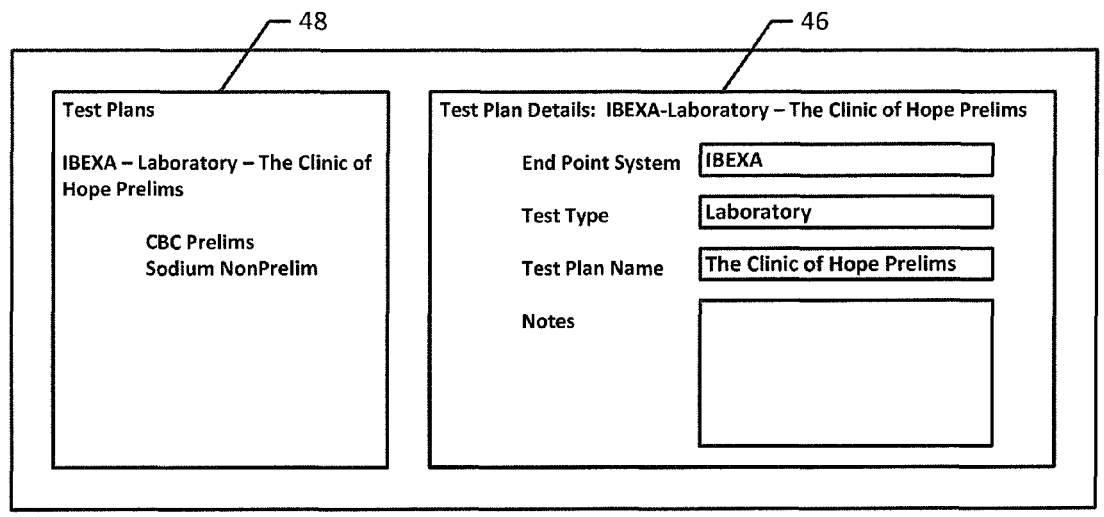
Figure 6:
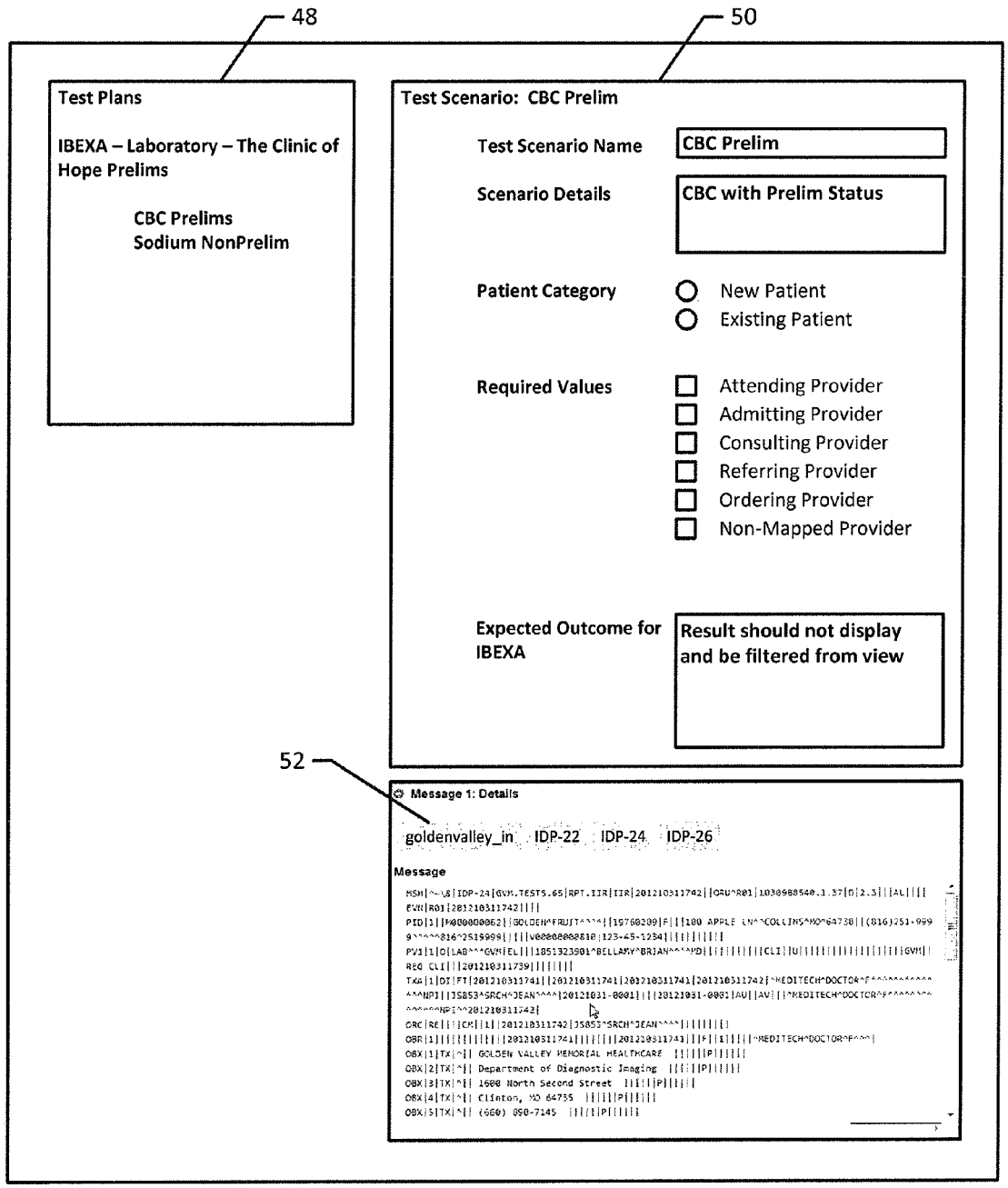
Figure 9:
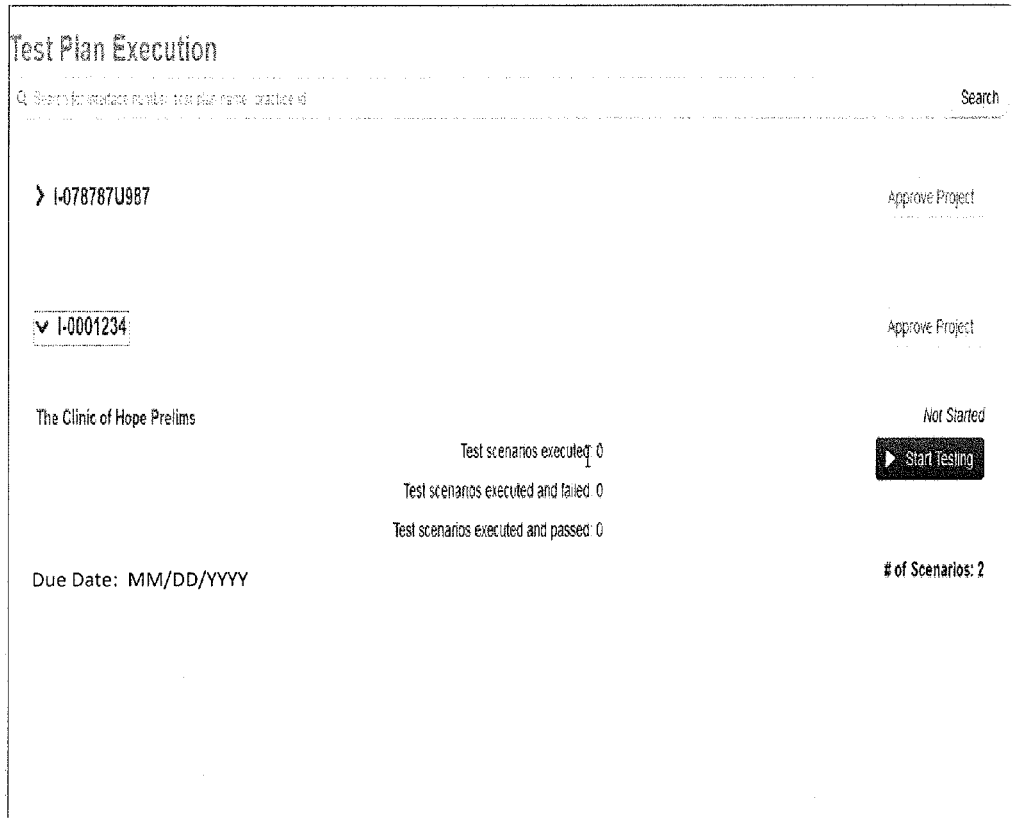
Figure 11:

Having thus described certain embodiments of the invention in general terms, reference will now be made to the accompanying drawings, which are not necessarily drawn to scale, and wherein:

FIG. 1 is a block diagram illustrating a plurality of source systems, a plurality of end points and an interface configured to support communication therebetween in accordance with an example embodiment of the present invention;

FIG. 2 is a block diagram of a computing device that may be embodied by or associated with the interface of FIG. 1 in accordance with an example embodiment of the present invention;

FIG. 3 is a flowchart illustrating operations performed, such as by a computing device of FIG. 2, in accordance with an example embodiment of the present invention;

FIG. 4 is a representation of a graphical user interface that facilitates the definition of an interface project in accordance with an example embodiment of the present invention;

FIG. 5 is a representation of a graphical user interface that facilitates the definition of a test plan in accordance with an example embodiment of the present invention;

FIG. 6 is a representation of a graphical user interface that permits the definition of a test scenario in accordance with an example embodiment of the present invention;

FIG. 7 is a representation of a graphical user interface that depicts the interface project following the addition of a test plan and test scenarios in accordance with an example embodiment of the present invention;

FIG. 8 is a representation of a graphical user interface that permits a test scenario to be created by the addition of messages in accordance with an example embodiment of the present invention;

FIG. 9 is a representation of a graphical user interface illustrating the execution status of one or more test plans in accordance with an example embodiment of the present invention;

Figure 10:
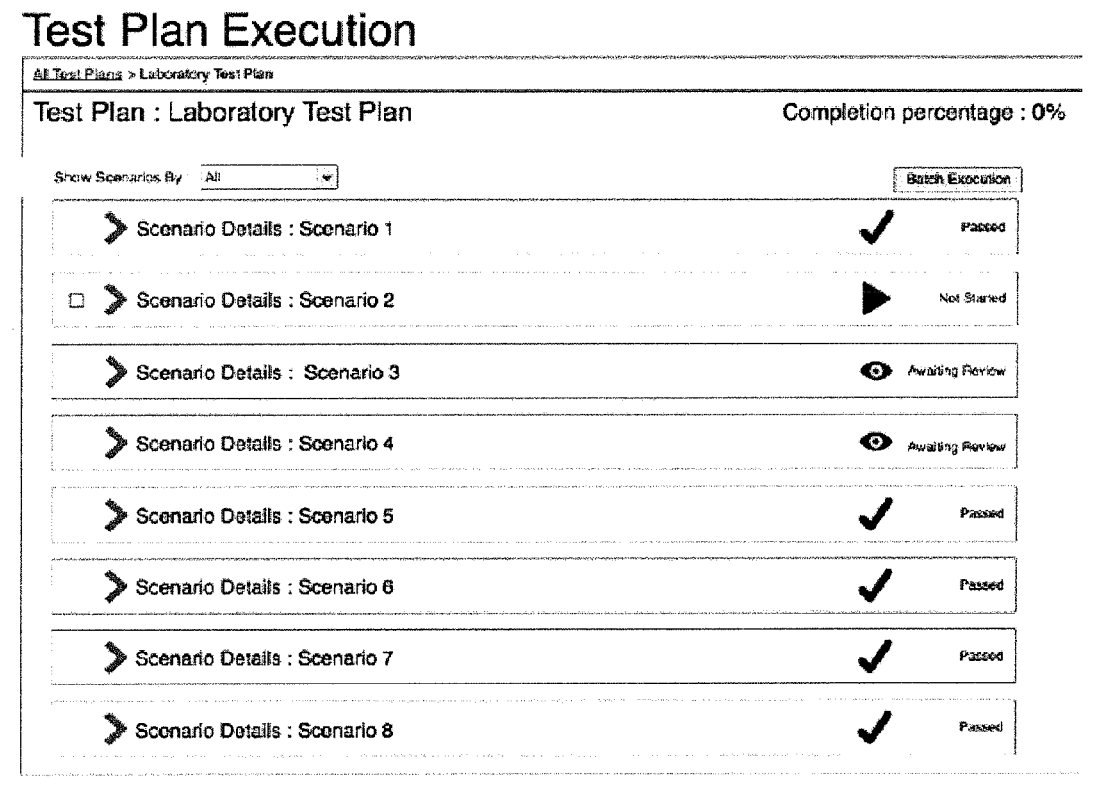

FIG. 10 is a representation of a graphical user interface illustrating the execution status of a plurality of test scenarios in accordance with an example embodiment of the present invention; and FIG. 11 is a representation of a graphical user interface illustrating the execution status of a plurality of test scenarios and depicting the review of test scenarios 3 and 4 in accordance with an example embodiment of the present invention.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The provision of healthcare frequently requires a plurality of different systems to communicate. For example, various physician practices and various laboratories must frequently communicate to permit the physician practices to order tests and for the laboratories to report the results of those tests. As such, the various healthcare systems frequently exchange messages, such as messages including orders, laboratory results and the like. The messages are frequently captured in an electronic health record of the patient which may be, for example, maintained or otherwise accessible by the physician practice. The messages may have any one of a variety of predefined formats including formats defined by the Continuity of Care document (CCD) and/or the fast healthcare interoperability resources (FHIR). However, the messages are commonly formatted in accordance with the health level 7 (HL7) standard, so as to be referred to as HL7 messages.

One example of a system that may facilitate the exchange of electronic messages between various healthcare systems is shown in FIG. 1. In this example, four different laboratories 10 are configured to communicate with two different physician practices 12. However, a system may include more or fewer healthcare systems and different types of healthcare systems. As shown in FIG. 1, the healthcare systems do not communicate directly with one another, but communicate via an interface 14 that serves as an intermediary between the various healthcare systems. The interface performs a variety of functions including routing of the messages and insuring that the messages are properly formatted. The interface may also communicate with a storage device, such as cloud storage 16, in order to store test messages to be exchanged between the healthcare systems.

The interface 14 may be configured in various manners, but in one embodiment, the interface includes or is otherwise associated with a computing device 20, such as a computer workstation, a server or the like, as shown in FIG. 2. In this embodiment, the computing device that is embodied by or otherwise associated with the interface may include or otherwise be in communication with processing circuitry 21 that is configurable to perform actions in accordance with one or more example embodiments disclosed herein. In this regard, the processing circuitry may be configured to perform and/or control performance of one or more functionalities of the computing device in accordance with various example embodiments, and thus may provide means for performing functionalities of the computing device. The processing circuitry may be configured to perform data processing, application execution and/or other processing and management services according to one or more example embodiments.

In some example embodiments, the processing circuitry 21 may include a processor 22 and, in some embodiments, such as that illustrated in FIG. 2, may further include memory 24. The processing circuitry may be in communication with or otherwise control a communication interface 26 and, in some embodiments, a user interface 28. As such, the processing circuitry may be embodied as a circuit chip (e.g., an integrated circuit chip) configured (e.g., with hardware, software or a combination of hardware and software) to perform operations described herein.

The processor 22 may be embodied in a number of different ways. For example, the processor may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. Although illustrated as a single processor, it will be appreciated that the processor may comprise a plurality of processors. The plurality of processors may be in operative communication with each other and may be collectively configured to perform one or more functionalities of the computing device 10 as described herein. The plurality of processors may be embodied on a single computing device or distributed across a plurality of computing devices collectively configured to function as the computing device. In some example embodiments, the processor may be configured to execute instructions stored in the memory 24 or otherwise accessible to the processor. As such, whether configured by hardware or by a combination of hardware and software, the processor may represent an entity (e.g., physically embodied in circuitry—in the form of processing circuitry 21) capable of performing operations according to embodiments of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform one or more operations described herein.

In some example embodiments, the memory 24 may include one or more non-transitory memory devices such as, for example, volatile and/or non-volatile memory that may be either fixed or removable. In this regard, the memory may comprise a non-transitory computer-readable storage medium. It will be appreciated that while the memory is illustrated as a single memory, the memory may comprise a plurality of memories. The plurality of memories may be embodied on a single computing device or may be distributed across a plurality of computing devices collectively configured to function as the computing device 20. The memory may be configured to store information, data, applications, instructions and/or the like for enabling the computing device to carry out various functions in accordance with one or more example embodiments. For example, the memory may be configured to buffer input data for processing by the processor 22. Additionally or alternatively, the memory may be configured to store instructions for execution by the processor. As yet another alternative, the memory may include one or more databases that may store a variety of files, contents or data sets, such as electronic health records for a plurality of patients. Among the contents of the memory, applications may be stored for execution by the processor in order to carry out the functionality associated with each respective application. In some cases, the memory may be in communication with one or more of the processor, user interface 28, or communication interface 26 via a bus or buses for passing information among components of the computing device.

The user interface 28 may be in communication with the processing circuitry 21 to receive an indication of a user input at the user interface and/or to provide an audible, visual, mechanical or other output to the user. As such, the user interface may include, for example, a keyboard, a mouse, a joystick, a display, a touch screen display, a speaker and/or other input/output mechanisms. In embodiments in which the computing device 20 is implemented on a server or other network device, aspects of the user interface may be limited, or the user interface may even be eliminated. For example, the computing device may act as a server or host device, with a user interface provided by a client application.

The communication interface 26 may include one or more interface mechanisms for enabling communication with other devices and/or networks, such as with one or more source systems 10 and one or more end points 12. In some cases, the communication interface may be any means such as a device or circuitry embodied in either hardware, or a combination of hardware and software that is configured to receive and/or transmit data from/to a network and/or any other device or module in communication with the processing circuitry 21. By way of example, the communication interface may be configured to enable the computing device 20 to communicate with a server or other network device via a wireless network, such as a wireless local area network (WLAN), cellular network, and/or the like. Additionally or alternatively, the communication interface may be configured to enable the computing device to communicate with the server or other network device via a wireline network. In some example embodiments, the communication interface may be configured to enable communication between the computing device and one or more servers or other network devices via the Internet. Accordingly, the communication interface may, for example, include an antenna (or multiple antennas) and supporting hardware and/or software for enabling communications with a wireless communication network (e.g., a wireless local area network, cellular network, and/or the like) and/or a communication modem or other hardware/software for supporting communication via cable, digital subscriber line (DSL), universal serial bus (USB), Ethernet or other methods.

Having now described computing device 20 configured to implement and/or support implementation of various example embodiments, features of several example embodiments will now be described. It will be appreciated that the following features are non-limiting examples of features provided by some example embodiments. Further, it will be appreciated that embodiments are contemplated within the scope of disclosure that implement various subsets or combinations of the features further described herein. Accordingly, it will be appreciated that some example embodiments may omit one or more of the following features and/or implement variations of one or more of the following features.

Referring now to FIG. 3, the operations performed, such as by the computing device 20 of FIG. 2, in order to implement a test plan including the transmission of test messages are described. In this regard, prior to the exchange of messages between a source system 10 and an end point 12, such as between a laboratory and a physician practice, the interface 14 that is positioned intermediate the source system and end point is advantageously tested, such as by the exchange of test messages between the source system and end point to ensure that the interface is functioning properly and that messages may be properly exchanged between the source system and the end point. In accordance with an example embodiment, a plurality of test messages are collected from each of the various source systems. As shown in block 30 of FIG. 3, the computing device and, more particularly, the processing circuitry 21, such as the processor 22, the memory 24 or the like, is configured to store the plurality of test messages from each of the plurality of different source systems. In regards to the embodiment of FIG. 1, the computing device may store the plurality of test messages in cloud storage 16. However, the test messages may be stored in other locations, such as the memory of the computing device or another memory device associated with and in communication with the processor or the computing device.

The test messages from the plurality of different source systems 10 are generally of the same type as the messages that will be exchanged between the source system and the end point 12 during normal communication between the source system and the end point following verification of the interface 14. For example, a laboratory that performs a variety of blood tests may provide test messages indicative of the various results, including both positive, negative and indeterminate results, that may be provided. In addition, the test messages that are provided and, in turn, are stored, are of the type that are to be captured in an electronic health record, such as an electronic health record maintained or otherwise accessible by a physicians practice or the like. In one example, the test messages may be provided in accordance with the HL7 standard. Each test message generally includes a variety of data fields including, for example, an identification of the source system and the end point, an identification of the type of test and the result and an identification of the patient.

In accordance with an example embodiment, the test messages may be provided in advance of an actual test of the interface 14. As such, the source system 10 may provide the test messages during a period of time in which it is more convenient for the source system and the test messages may then be stored until a subsequent time at which the test is executed as described below. Thus, the method, computing device and computer program product of an example embodiment simplify the coordination associated with the performance of a test of an interface by permitting the test messages to be provided and stored in advance and eliminating or at least reducing the need for the source system to actively participate at the time that the test is to be executed by the end point 12.

As shown in block 34 of FIG. 3, the computing device 20, such as the processing circuitry 21, e.g., the processor 22, the user interface 28 or the like, is also configured to construct a test plan. The test plan identifies the end point 12, such as a physician practice and/or the electronic health record vendor of the physician practice, that is to receive the test messages upon execution of the test plan by the end point. The test plan also includes one or more test messages that have been previously stored as well as the anticipated outcomes at the end point following transmission of each of the one or more test messages. The anticipated outcome may include the modification of the electronic health record of a patent. A test message may have various anticipated outcomes depending upon the type of test message. For example, some test messages that report the result of a laboratory test may have an anticipated outcome of the test result being recorded in the electronic health record of the patient and an indication being provided as to whether the test result passed, failed or was indefinite. Other test messages may seek to establish a new patient record with the anticipated outcome therefore being the creation of an electronic health record for a new patient. Still further, other test messages may be designed to overwrite prior results with the anticipated outcome therefore being the replacement of a prior result in the electronic health record with a different result provided by the test message.

The test plan may be constructed in various manners. In one example, a test plan may be created in order to test an interface 14 by initially defining an interface project. As shown in FIG. 4, for example, an interface project, e.g., interface project I-0001234, may be at least partially defined by the entry of information via a graphical user interface 42. The interface project may include a variety of fields including, for example, the project manager, the interface number, a description of the interface project, the interface type, the health system, the source system. 10, the end point system 12 and the practice identifier (ID). Further, the interface project may define testing dates to define a window during which the end point is expected to execute the test plan in order to determine whether the interface is functioning properly. In this regard, a start date and a due date may be defined. Further, the test plan and test scenarios that are to be executed as part of the interface project may be identified in the field designated 44. In the example of FIG. 4, the test plan and test scenarios have not yet been defined such that no such test plan and test scenarios are identified.

In one embodiment, a test plan may be defined by initially identifying the test plan and then identifying and defining the one or more test scenarios that comprise the test plan. As shown in FIG. 5, for example, a test plan may be defined by the entry of information via a graphical user interface that identifies the end point system 12, the type of test and the name of the test plan in the right panel 46. In this example, the end point system is IBEXA, the test type is a laboratory test and the name of the test plan is the Clinic of Hope Prelims. As indicated in the left panel 48 of the graphical user interface of FIG. 5, this test plan may include two test scenarios, that is, CBC Prelims and Sodium NonPrelim. Although a test plan having two test scenarios is illustrated, a test plan may alternatively include a single test scenario or any number of test scenarios.

The test scenarios that comprise the test plans may also be defined in various manners. One example of the definition of a test scenario is shown in FIG. 6 in which the CBC Prelim test scenario is defined in the right panel 50. As exemplified by the graphical user interface of FIG. 6, the test scenario may be defined so as to have a name and, if desired, details or notes regarding the test scenario. The test scenario of this example also identifies the patient category, such as a new patient or an existing patient, and identifies the type of provider, such as an attending provider, admitting provider, consulting provider, referring provider, ordering provider or non-mapped provider, who has ordered the test. The expected outcome for the test scenario is also identified. In this regard, the expected outcome is from the perspective of the end point system 12 and, more particularly, from the perspective of the manner in which the electronic health record of the patient will be modified as a result of execution of the test scenario. In this example, the expected outcome from the proper execution of the CBC Prelim test scenario is that the result should not display, but should be filtered from view within the electronic health record of the patient.

The test scenario is also constructed so as to include one or more test messages. In this regard, the text of each test message may be included in the test scenario, such as within the message details portion of the test scenario. The test scenario may include one or any other number of test messages that may be executed, such as in a sequential fashion, with the anticipated outcome being the outcome that is anticipated following execution of each of the test messages of the test scenario. A test scenario may be created or defined, such as in the manner described above in conjunction with the entry of information via the graphical user interface of FIG. 6, for each of the test scenarios of the test plan.

As shown in FIG. 6, one or more tags 52 may be associated with a test message. In this regard and as indicated in block 32 of FIG. 3, the computing device 20, such as the processing circuitry 21, e.g., the processor 22, the user interface 28 or the like, may be configured to associate tags with respective test messages. The tags may be associated with a respective test message by an administrator or other user who is designing the test plan or otherwise evaluating the test messages. Alternatively, the tags may be associated with a respective test message in an automated manner, such as based upon the content of the test message, the type of test scenario or test plan, the type of source system 10 or end point 12 or the like. Various different types of tags may be associated with the test message. For example, the tags may identify a particular source system, a particular end point, a particular type of test, a particular anticipated outcome or the like.

In the foregoing discussion regarding the definition of a test scenario in conjunction with the example embodiment of the graphical user interface of FIG. 6, the test scenario was described to include one or more test messages. The test messages to be included in a test scenario may be identified in various manners. For example, the administrator or other user designing the test plan may review the plurality of test messages previously provided by the source system 10 for which the test plan is designed. From these test messages, the administrator or other user may identify one or more test messages that are appropriate for the respective test scenario. Alternatively, the computing device 20 and, more particularly, the processing circuitry 21, such as the processor 22, the memory 24 or the like, may select the test messages from among the plurality of test messages previously provided by the source system and now stored with the processing circuitry being configured to identify those test messages having one or more particular tags associated therewith. In this embodiment, each of the test messages having the one or more particular tags may then be included in the test scenario and the administrator or other user who is designing the test plan may review this more limited subset of test messages provided by the source system and select from among the test messages that have been identified to include the one or more particular tags to be included within the test scenario.

Following the definition of the test plan and the one or more test scenarios that comprise a test plan, the interface project may be updated so as to include the test plan and, as a result the one or more test scenarios that comprise the test plan. With reference to FIG. 7, the example of the interface project described above in conjunction with the FIG. 4 is again depicted with the test plan and test scenarios that have now been defined as described above in conjunction with FIGS. 5 and 6 now being included in field 44 of the graphical user interface 42 of interface project I-0001234. As illustrated, the name of the test plan and the test scenarios may be presented, along with the expected outcome of each test scenario and/or the status of each test scenario, such as executed, passed, failed, not yet executed, etc.

The test plan and test scenarios may be constructed in various manners. In the foregoing example, a test plan and test scenarios were defined and one or more test messages were then selected and added to the predefined test scenario. Alternatively, one or more test messages may be initially selected and a test scenario and, in turn, a test plan may then be constructed around the selected test messages so as to include those test messages. In this embodiment, FIG. 8 illustrates that the plurality of test messages that have been previously provided by a source system 10, e.g., source system IDP-24-GVM, and are currently stored, such as by cloud storage 16, may be displayed within a graphical user interface. For each test message, the text of the test message as well as the tags 52 associated with the test message may be presented. In one embodiment, one or more additional tags may be associated with a respective message, such as by selecting the "add a tag" link and then entering the information necessary to add a respective tag. In addition, each message may have a respective status. A legend identifying the different types of status recognized in this example embodiment is shown in FIG. 8. The different types of status include, for example, F=final, P=preliminary, C=corrected and X=cancelled.

As shown in FIG. 8, an administrator or other user constructing a test scenario may select (or unselect) all of the messages that have been previously provided by the source system 10. Alternatively, one or more individual test messages may be selected. Regardless of the manner in which a selection is made, the one or more selected test messages are included in a test scenario for the respective source system. The administrator or other user who is defining the test scenario may then provide the other information associated with the test scenario, such as described above in conjunction with the graphical user interface of FIG. 6.

Following its construction, a test plan may then be executed in order to test the exchange of messages between the source system 10 and the end point 12 identified by the interface project including testing of the operation of the interface 14 therebetween. In order to execute a test plan, the one or more test messages that comprise a test scenario of the test plan are transmitted, such as at the direction of the end point. In this regard, the test messages need not be transmitted by the source system as the source system has already provided the test messages and the test messages have been stored. Instead, the computing device 20, such as the processing circuitry 21, e.g., the processor 22, the communication interface 26 or the like, may be configured to cause the test messages to be retrieved from storage and to be transmitted to the end point. See block 36 of FIG. 3. As such, the source system need not necessarily participate at the time that the test plan is being executed so as to simplify the coordination between the various health care systems at the time of execution of the test plan. In at least some embodiments, the test messages that are transmitted cross both network and business boundaries during execution of the test plan, exactly as messages would in real production transactions and conversations, thereby permitting the real production data path to be tested. In order to cross the boundary, the test messages may flow through several translation layers, network filters and/or other secure networking technologies including, for example, a virtual private network (VPN) and optionally including encryption, file transfer protocol (FTP) and/or batching. Execution of the test plan advantageously permits these translation layers and network filters to be tested without any knowledge of their implementation. Thus, the method, computing device and computer program product of an example embodiment may permit communication between disparate systems to be tested over the same network, e.g., the same secure network, that will be utilized for the real production data path.

Following transmission of the test messages, a representative of the end point 12 may determine if the anticipated outcome associated with the respective test message has occurred. In an embodiment in which the anticipated outcome following the execution of a test message involves the modification of the electronic health record of a respective patient, the representative of the end point may review the electronic health record of the patient and determine if the electronic health record has been modified in the manner that is anticipated. For example, a screen shot, video or other representation of the anticipated modification of the electronic health record may be provided to the end point to facilitate the review of the electronic health record and the formulation of feedback regarding its modification. The representative of the end point may then provide feedback that is received by the computing device 20, such as the processing circuitry 21, e.g., the processor 22, the communication interface 26 or the like, regarding the outcome of the respective test message. See block 38 of FIG. 3. The feedback may indicate that the actual outcome matches or did not match the anticipated outcome. Alternatively, the feedback may be provided in other manners, such as by providing the electronic health record or a portion thereof of the respective patient such that the computing device, such as the processing circuitry, can evaluate the electronic health record and determine if the anticipated outcome occurred.

The computing device 20 and, more particularly, the processing circuitry 21, such as the processor 22, may also be configured to determine whether a test scenario executed properly, as in an instance in which the anticipated outcome of each test message was observed, or not. Additionally, the computing device and, more particularly, the processing circuitry, such as the processor, may determine whether the test plan that has been executed was successful based on the feedback. See block 40 of FIG. 3. In this regard, the processing circuitry may be configured to determine that a test plan successfully executed in an instance in which each of the test scenarios of the test plan successfully executed by having the anticipated outcome actually occur for each test message of each test scenario. Conversely, the processing circuitry may be configured to determine that a test plan failed based on the feedback in an instance in which any one of the test scenarios failed, such as by a test message of a test scenario not producing the anticipated outcome. In an instance in which a test plan was successfully executed, the test of the interface 14 may proceed or otherwise be successfully concluded. However, in an instance in which a test plan is determined not to have successfully executed, the communication between the source system 10 and the end point 12 may be further evaluated in order to determine the source of the issue and to remedy the issue such that subsequent test messages produce the anticipated outcome prior to indicating that the interface has passed the test.

In regards to the execution of a test plan, the end point 12, such as a physician practice and/or the electronic health record vendor of the physician practice, may trigger the execution of the test plan such that the test plan is executed at a time that is convenient for the end point with the computing device 20 embodied by or associated with the interface 14 being responsive to the triggering input from the end point. The end point may separately execute each test plan. For a test plan that includes multiple test scenarios, the end point may also separately execute each test scenario. Thus, the end point may cause one or more test scenarios to be executed while deferring execution of one or more other test scenarios. As such, the end point is provided with substantial control and flexibility regarding the manner and timing with which the test plans are executed. In order to permit an end point to readily determine the status of various test plans to be executed with respect to the end point, the computing device, such as the processing circuitry 21, e.g., the processor 22, the communication interface 26 or the like, may be configured to provide a graphical user interface that identifies each of the test plans to be executed as well as details associated with the execution of those test plans.

By way of example, FIG. 9 depicts a graphical user interface that may be provided by the computing device 20 and reviewed by or at the end point 12. In this regard, each test plan awaiting execution by the end point is identified, such as I-078787U987 and I-0001234. A representative of the end point may obtain additional information regarding one or more of these test plans, such as by selecting the link associated with a respective test plan. As shown in FIG. 9, further details regarding the test plan I-0001234 are provided including the number of scenarios, the number of scenarios that have been executed, the number of scenarios that have been executed and failed and the number of scenarios that have been executed and passed. In addition, a link or other input that permits the representative of the end point to begin testing of a respective test plan is provided. Further, the due date for completion of execution of the various test plans is also identified as a reminder to the end point.

In an example embodiment, the computing device 20 and, more particularly, the processing circuitry 21, such as the processor 22, may also provide more specific information regarding the status of each scenario of a test plan. As shown in the graphical user interface of FIG. 10, an end user may evaluate the status of each of the eight test scenarios associated with a laboratory test plan. As will be noted, test scenarios 1 and 5-8 have passed, test scenario 2 has not started and test scenarios 3 and 4 are have been executed and are awaiting review to determine if the anticipated outcome was achieved. As the test plan does not pass until all of the test scenarios have passed, the completion percentage for the laboratory test plan is also shown to be 0% in the example of FIG. 10.

For a test scenario that has been executed and is now awaiting review, the graphical user interface of FIG. 10 may also include a link or other input to permit the administrator or other user to provide the requisite review. In response to this input, a graphical user interface of the type shown in FIG. 11 may be provided in accordance with one example embodiment. In this example, the anticipated outcomes for test scenarios 3 and 4 which are awaiting review are provided and buttons or other forms of input are provided to permit the administrator or other user to indicate whether the anticipated outcome actually occurred or not. As will be apparent, there are many different ways of providing information regarding the execution of a test plan and the test scenarios with FIGS. 9-11 provided by way of example, but not of limitation.

A method, computing device 20 and computer program product are therefore provided in order to implement a test plan in an efficient manner. In this regard, the method, computing device and computer program product may permit a plurality of test messages to be stored in advance of the execution of the test plan such that the test plan may thereafter be executed without requiring the concurrent participation of members from both the source system 10 and the end point 12. As a result, the method, computing device and computer program product may permit an interface 14 to be tested pursuant to a test plan in a manner that creates less of an imposition upon the participants. Further, the method, computing device and computer program product of an example embodiment may provide for the comprehensive testing of an interface, both initially and thereafter, such as in response to a system upgrade, as opposed to the provision of a unit testing framework, a test harness or a regression tool.

As described above, FIG. 3 illustrates a flowchart of a system, method, and computer program product according to example embodiments of the invention. It will be understood that each block of the flowchart, and combinations of blocks in the flowchart, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices 24 of a computing device 20 and executed by processing circuitry 22 in the computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks or steps of the flowchart support combinations of means for performing the specified functions and combinations of steps for performing the specified functions. It will also be understood that one or more blocks of the flowchart, and combinations of blocks in the flowchart, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processing circuitry 22 may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. For example, the graphical user interfaces of FIGS. 4-11 are provided by way of example, but not of limitation, as the same general type of information may be collected and provided in various different manners in other embodiments. Additionally, while a test plan involving messages originating with a laboratory that are transmitted to a physician practice has been described by way of example, the method, computing device and computer program product of an example embodiment may support the execution of test plans involving test messages transmitted between a wide variety of different source systems and end points including test messages originating with a physician practice that are transmitted to a laboratory during execution of a test plan. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method comprising:
   storing a plurality of test messages from each of a plurality of different source systems, wherein the plurality of test messages comprise test messages to be captured in an electronic health record;
   constructing, with processing circuitry, an interface project that identifies, a source system, an end point and an indication of the interface type of an interface connecting the source system and end point and that includes a test plan comprised of one or more test scenarios, each of which includes one or more test messages, wherein constructing an interface project comprises constructing a test plan identifying an end point and comprising one or more test messages that have been previously stored and respective anticipated outcomes of each test scenario at the end point following transmission to the end point of the one or more test messages, wherein the anticipated outcomes include modification of an existing electronic health record in response to the test message and creation of an electronic health record for a new patient in response to the test message,
   wherein constructing the test plan comprises identifying with the processing circuitry, based upon tags associated with the respective test messages, one or more test messages that have been previously provided by the source system and that have been previously stored and then receiving a selection by a user from among the one or more test messages one or more test messages that are to be included in the test plan, wherein the tags are configured to identify the source system, the end point, a type of test and the anticipated outcome;
   in response to a trigger provided by a particular end point following selection of one or more test plans from a presentation, at the particular end point, of a graphical user interface that allows selection of the one or more test plans awaiting execution by the particular end point, executing the one or more selected test plans by transmitting the one or more test messages of the one or more selected test plans to the end point without participation of the plurality of source systems at the time of test plan execution as a result of prior storage of the plurality of test messages;
   receiving feedback regarding the outcome following transmission of the one or more test messages of the one or more selected test plans to the end point; and
   determining whether the one or more selected test plans were successfully executed based upon the feedback.

2. A method according to claim 1 wherein the respective anticipated outcomes comprise respective anticipated modifications to the electronic health record.

3. A method according to claim 1 wherein the test plan comprises a plurality of test scenarios, and wherein transmitting the one or more messages of the test plan comprises transmitting the one or more test messages of at least one test scenario of the test plan and deferring transmission of the one or more test messages of another test scenario of the test plan.

4. A method according to claim 1 wherein the test messages comprise Health Level 7 (HL7), Continuity of Care document (CCD) or fast healthcare interoperability records (FHIR) test messages.

5. A method according to claim 1 further comprising providing a representation of the electronic health record that is anticipated following transmission of the one or more test messages of the test plan to the end point prior to receipt of the feedback.

6. A method according to claim 1 wherein constructing the test plan comprises identifying a patient category and a type of provider.

7. A method according to claim 1 wherein transmitting the one or more test messages comprises transmitting the one or more test messages across both network and business boundaries during execution of the test plan such that the one or more test messages flow through one or more of a translation layer, a network filter or a secure networking technology.

8. A method according to claim 1 further comprising providing the end point with a representation of the electronic health record that is anticipated following transmission of the one or more test messages of the test plan to the end point prior to receipt of feedback from the end point.

9. A method according to claim 1 wherein the feedback comprises an indication as to whether the outcome matches the electronic health record that is anticipated.

10. A computing device comprising processing circuitry configured to:
   cause storage of a plurality of test messages from each of a plurality of different source systems, wherein the plurality of test messages comprise test messages to be captured in an electronic health record;
   construct an interface project that identifies a source system, an end point and an indication of the interface type of an interface connecting the source system and end point and that includes a test plan comprised of one or more test scenarios, each of which includes one or more test messages and respective anticipated outcomes at the end point following transmission of the one or more test messages, wherein the test plan identifies an end point and comprises one or more test messages that have been previously stored and respective anticipated outcomes of each test scenario at the end point following transmission to the end point of the one or more test messages, wherein the anticipated outcomes include modification of an existing electronic health record in response to the test message and creation of an electronic health record for a new patient in response to the test message, wherein constructing the test plan comprises identifying with the processing circuitry, based upon tags associated with the respective test messages, one or more test messages that have been previously provided by the source system and that have been previously stored and then receiving a selection by a user from among the one or more test messages of the one or more test messages that are to be included in the test plan, wherein the tags are configured to identify the source system, the end point, a type of test and the anticipated outcome;

in response to a trigger provided by a particular end point following selection of one or more test plans from a presentation, at the particular end point, of a graphical user interface that allows selection of the one or more test plans awaiting execution by the particular end point, execute the selected one or more test plans by causing transmission of the one or more test messages of the one or more selected test plans to the end point without participation of the plurality of source systems at the time of test plan execution as a result of prior storage of the plurality of test messages;

receive feedback regarding the outcome following transmission of the one or more test messages of the one or more selected test plans to the end point; and determine whether the one or more selected test plans were successfully executed based upon the feedback.

11. A computing device according to claim 10 wherein the respective anticipated outcomes comprise respective anticipated modifications to the electronic health record.

12. A computing device according to claim 10 wherein the test plan comprises a plurality of test scenarios, and wherein the processing circuitry is configured to cause transmission of the one or more messages of the test plan by causing transmission of the one or more test messages of at least one test scenario of the test plan and deferring transmission of the one or more test messages of another test scenario of the test plan.

13. A computing device according to claim 10 wherein the test messages comprise Health Level 7 (HL7), Continuity of Care document (CCD) or fast healthcare interoperability records (FHIR) test messages.

14. A computing device according to claim 10 wherein the processing circuitry is further configured to provide a representation of the electronic health record that is anticipated following transmission of the one or more test messages of the test plan to the end point prior to receipt of the feedback.

15. A computing device according to claim 10 wherein the processing circuitry is configured to construct the test plan by identifying a patient category and a type of provider.

16. A computing device according to claim 10 wherein the processing circuitry is configured to transmit the one or more test messages by transmitting the one or more test messages across both network and business boundaries during execution of the test plan such that the one or more test messages flow through one or more of a translation layer, a network filter or a secure networking technology.

17. A computing device according to claim 10 wherein the processing circuitry is further configured to provide the end point with a representation of the electronic health record that is anticipated following transmission of the one or more test messages of the test plan to the end point prior to receipt of feedback from the end point.

18. A computing device according to claim 10 wherein the feedback comprises an indication as to whether the outcome matches the electronic health record that is anticipated.

19. A computer program product comprising a non-transitory computer readable medium having program code stored thereon, the program code comprising program code instructions configured, upon execution, to:

cause storage of a plurality of test messages from each of a plurality of different source systems, wherein the plurality of test messages comprise test messages to be captured in an electronic health record;

construct an interface project that identifies a source system, an end point and an indication of the interface type of an interface connecting the source system and end point and that includes a test plan comprised of one or more test scenarios, each of which includes one or more test messages and respective anticipated outcomes at the end point following transmission of the one or more test messages, wherein the test plan identifies an end point and comprises one or more test messages that have been previously stored and respective anticipated outcomes of each test scenario at the end point following transmission to the end point of the one or more test messages, wherein the anticipated outcomes include modification of an existing electronic health record in response to the test message and creation of an electronic health record for a new patient in response to the test message, wherein constructing the test plan comprises identifying one or more test messages, based upon tags associated with the respective test messages, that have been previously provided by the source system and that have been previously stored and then receiving a selection by a user from among the one or more test messages of the one or more test messages that are to be included in the test plan, wherein the tags are configured to identify the source system, the end point, a type of test and the anticipated outcome;

in response to a trigger provided by a particular end point following selection of one or more test plans from a presentation, at the particular end point, of a graphical user interface that allows selection of the one or more test plans awaiting execution by the particular end point, execute the one or more selected test plans by causing transmission of the one or more test messages of the one or more selected test plans to the end point without participation of the plurality of source systems at the time of test plan execution as a result of prior storage of the plurality of test messages;

receive feedback regarding the outcome following transmission of the one or more test messages of the one or more selected test plans to the end point; and determine whether the one or more selected test plans were successfully executed based upon the feedback.

20. A computer program product according to claim 19 wherein the respective anticipated outcomes comprise respective anticipated modifications to the electronic health record.

21. A computer program product according to claim 19 wherein the test plan comprises a plurality of test scenarios, and wherein the program code instructions configured to cause transmission of the one or more messages of the test plan comprise program code instructions configured to cause transmission of the one or more test messages of at least one test scenario of the test plan and to defer transmission of the one or more test messages of another test scenario of the test plan.

22. A computer program product according to claim 19 wherein the program code instructions configured to transmit the one or more test messages comprise program instructions configured to transmit the one or more test messages across both network and business boundaries during execution of the test plan such that the one or more test messages flow through one or more of a translation layer, a network filter or a secure networking technology.

23. A computer program product according to claim 19 wherein the program code further comprises program code instructions configured, upon execution, to provide the end point with a representation of the electronic health record that is anticipated following transmission of the one or more test messages of the test plan to the end point prior to receipt of feedback from the end point.

24. A computer program product according to claim 19 wherein the feedback comprises an indication as to whether the outcome matches the electronic health record that is anticipated.

* * * * *